(12) United States Patent
Kopelman et al.

(10) Patent No.: US 7,536,234 B2
(45) Date of Patent: May 19, 2009

(54) METHOD AND SYSTEM FOR MANUFACTURING A DENTAL PROSTHESIS

(75) Inventors: Avi Kopelman, Ramat Chen (IL); Eldad Taub, Reut (IL)

(73) Assignee: Cadent Ltd., Or Yehuda (IL)

( * ) Notice: Subject to any disclaimer, the term of this patent is extended or adjusted under 35 U.S.C. 154(b) by 0 days.

(21) Appl. No.: 11/046,709

(22) Filed: Feb. 1, 2005

(65) Prior Publication Data

US 2005/0177266 A1  Aug. 11, 2005

Related U.S. Application Data

(60) Provisional application No. 60/542,327, filed on Feb. 9, 2004.

(51) Int. Cl.
*G06F 19/00* (2006.01)
*A61C 5/10* (2006.01)

(52) U.S. Cl. .................. 700/118; 700/173; 433/223

(58) Field of Classification Search ............... 700/117, 700/173, 163, 118; 433/222.1, 223
See application file for complete search history.

(56) References Cited

U.S. PATENT DOCUMENTS

| 4,663,720 | A | | 5/1987 | Duret et al. | |
|---|---|---|---|---|---|
| 4,928,221 | A | * | 5/1990 | Belkhiter | 700/86 |
| 4,937,928 | A | | 7/1990 | van der Zel | |
| 4,974,165 | A | * | 11/1990 | Locke et al. | 700/193 |
| 5,027,281 | A | | 6/1991 | Rekow et al. | |
| 5,378,154 | A | | 1/1995 | Van Der Zel | |
| 6,161,055 | A | * | 12/2000 | Pryor | 700/175 |
| 6,261,098 | B1 | * | 7/2001 | Persson | 433/213 |
| 6,912,446 | B2 | * | 6/2005 | Wang et al. | 700/193 |
| 2002/0076530 | A1 | | 6/2002 | MacDougald et al. | |

FOREIGN PATENT DOCUMENTS

| EP | 1 250 895 A2 | 10/2002 |
|---|---|---|
| WO | 02/09612 A1 | 2/2002 |

* cited by examiner

*Primary Examiner*—Ryan A Jarrett
(74) *Attorney, Agent, or Firm*—The Nath Law Group; Jerald L. Meyer; Derek Richmond

(57) ABSTRACT

A method and system are provided for manufacturing a dental prosthesis, in which the machining operations therefor may be optimized. Dimensional data of at least one critical parameter of the workpiece from which the crown is to be manufactured is determined and compared with corresponding target dimensional data of the desired prosthesis. The workpiece is then subjected to a material removal operation by a machining tool along machining paths that are determined on the basis of this comparison.

20 Claims, 7 Drawing Sheets

METHOD AND SYSTEM FOR MANUFACTURING A DENTAL PROSTHESIS

This application claims the benefit of prior U.S. provisional patent application No. 60/542,327 filed Feb. 9, 2004, the contents of which are hereby incorporated by reference in their entirety.

FIELD OF THE INVENTION

This invention relates to a method and system for manufacturing a dental prosthesis such as a crown or bridge, in particular based on computer controlled machining techniques.

BACKGROUND OF THE INVENTION

The manufacture of dental prostheses such as crowns and bridges needs to be as precise as possible in order to ensure that, externally, the crown fits within the area of the oral cavity assigned thereto. It is also important to ensure, of course, that internally, and also with respect to the margin line, the crown fits properly onto the preparation.

Referring to the external profile of the crown, the width of the crown must be such so as not to interfere with the adjacent teeth, and to thus maintain a reasonable interproximal gap on either side of the crown with neighboring teeth. Moreover a proper functional contact relationship needs to be established with respect to the surrounding teeth, both for static and dynamic conditions. Thus the heights and shapes of different parts of the crown must be controlled accordingly. Further, close fitting contact is also required between the lower edge of the crown and the finish line of the preparation to ensure long and trouble-free life for the prosthesis, which in turn requires the lower edge to follow closely the profile of the finish line. Manual manufacturing methods for dental prostheses typically require a number of "fitting and fixing" cycles in order to ensure that the crown is properly dimensioned before finally fixing the prosthesis to the preparation in the intraoral cavity.

CNC-based methods for manufacturing dental prostheses are known and represent a significant improvement in automating the manufacturing process to provide a high degree of dimensional accuracy. For example, in U.S. Pat. No. 4,663,720 and in U.S. Pat. No. 5,027,281, material is removed from a massive block of material by means of a CNC milling machine, and the machining paths are calculated from a 3D numerical model of prosthesis. In U.S. Pat. No. 4,937,928, a dental prosthesis is manufactured by successively applying a number of layers of material on a model in the shape of the part of the teeth where the prosthesis is to be provided. After each layer is applied, the workpiece is worked by a CNC tool controlled by a CAD/CAM system. In U.S. Pat. No. 5,378,154, a similar method is used for forming layers of material onto a preparation, machining each layer along paths that follow three dimensional irregularly spaced curved lines.

In each case, the machining paths are predefined without reference to the pre-machining geometry of the material layers.

SUMMARY OF THE INVENTION

In accordance with the present invention there are provided a method and system for manufacturing a dental prosthesis which enables the machining time to be optimized by determining dimensional data of at least one critical parameter of the workpiece, comparing this data with corresponding nominal or target dimensional data, and determining machining paths on the basis of this comparison.

The term "prosthesis" is herein taken to include onlays, such as crowns and bridges, for example, and inlays, such as caps, for example, and any other artificial partial or complete denture.

The terms "tool" and "machining tool" are taken herein to include any tool that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by computer means.

In one embodiment of the invention, a dental prosthesis is manufactured by performing a mapping operation to determine the three-dimensional shape of the outer surface of the material that is to be machined to form the prosthesis, either the final layer or any intermediate layer, and then subjecting the layer to a material removing operation, wherein the machining paths are computer controlled on the basis of the local differences between actual and required shape, and optimized to reduce machining times.

In another embodiment of the invention, a dental prosthesis is manufactured by performing a measuring operation to determine at least some critical dimensions of the outer surface of the prosthesis, either the final layer or any intermediate layer. These measurements are then compared to the corresponding nominal dimensions in which the crown is to be fitted, and then subjecting the layer to a material removing operation, wherein the machining paths are CNC controlled and optimized to reduce machining times.

Accordingly, the distance between adjacent machining paths may be maintained, for example in the order of 0.02-0.2 mm, and a optimal amount of material can be removed in each sweep without damaging the prosthesis and/or the tool. There is therefore no need to arrange machining paths within a fictitious envelope, as these paths are designed to match the actual external details of the workpiece before machining commences. Thus:

(a) potential damage to the prosthesis and/or tool by attempting to remove too much material in one sweep, as may happen if the material exceeds the limits of the envelope, is generally avoided; and, (b) machining time is not wasted by passing the tool across empty air for some portion of the machining paths, as may happen if the material is well below the limits of the envelope.

The term "layer" is used herein to a thickness of material overlying a core, as well as to a core of material that itself may or may not be overlying or underlying another layer of material.

The present invention thus relates to a method for manufacturing a dental prosthesis from a workpiece having at least one layer of a material, the method comprising for the or each layer:

a) providing actual dimensional data for at least one parameter associated with said layer;

b) for at least one said parameter, forming a comparison between said actual dimensional data and predetermined target dimensional data that it is desired to conform said parameter to; and c) subjecting said layer to at least one material removal operation by suitable machining means along machining paths which are a function of said comparison, such that after said operation the or each said parameter associated with the layer substantially conforms with said target dimensional data Optionally, at least one of the following steps may be provided providing said at least one layer of material prior to step (a); and/or providing said target dimensional data for said at least one parameter prior to step (b).

The layer of material may be a first, innermost layer of material deposited onto a physical model substantially identical to a tooth preparation onto which said prosthesis is to be mounted. In such a case, the method may further comprise the step of:

(y) providing an additional layer of material over said layer after step (c) and repeating steps (a) to (c) for said additional layer.

The prosthesis comprises a plurality of additional layers, and step (y) may be repeated for each one of said plurality of additional layers.

According to a first embodiment of the invention, and considering the outermost layer of a multi-layered prosthesis, or alternatively, the layer of a prosthesis having only one layer, said parameter is a geometric parameter comprising surface coordinates of said layer. The target dimensional data comprises the numerical values of the surface coordinates of an idealized or required outer surface of said prosthesis. The surface coordinates of said required outer surface are obtained from a library of crown and tooth outer surface profiles. The required outer surface is configured to fit within a predetermined control volume. The predetermined control volume is defined such as to provide at least one of:

adequate clearance between said prosthesis and adjacent teeth when the prosthesis is fixed onto the corresponding preparation in the intraoral cavity; and adequate occlusion between said prosthesis and teeth of the opposite jaw when the prosthesis is fixed onto the corresponding preparation in the intraoral cavity.

The control volume is determined by three-dimensional surface scanning of the intraoral cavity with a suitable probe in the vicinity of the area thereof in which the prosthesis is to be mounted.

The said actual dimensional data may comprise the actual surface coordinates of said layer prior to said operation. Step (a) of the method preferably comprises scanning said layer with a suitable three-dimensional surface probe. Such a probe preferably provides a three dimensional structure based on confocal imaging. Alternatively, the actual dimensional data may be obtained using any suitable intra oral scanning technique, based on optical methods, direct contact or any other means, applied directly to the patient's dentition. Alternatively, the data may be obtained using techniques based on scanning a positive and/or negative model of the intra oral cavity. Alternatively, X-ray based, CT based or any other type of scanning of the patient or of a positive and/or negative model of the intra-oral cavity. The dimensional data may be associated with a complete dentition, or of a partial dentition, for example such as the preparation only.

In a second embodiment of the invention, the said parameter is a geometric parameter comprising at least one linear dimension of said layer. The target dimensional data comprises the numerical values of at least one of the target width or target height of a location on the jaw on which the crown is to be fitted. The target width may include the mesiodistal size of a tooth that is being replaced, and may be defined such as to provide adequate clearance between said prosthesis and adjacent teeth when the prosthesis is fixed onto the corresponding preparation in the intraoral cavity. The target height may be defined such as to provide adequate occlusion between said prosthesis and teeth of the opposite jaw when the prosthesis is fixed onto the corresponding preparation in the intraoral cavity.

In another embodiment, said parameter is a geometric parameter comprising the profile of a lower edge of said prosthesis. This profile may be defined such as to provide close-fitting contact between said prosthesis and the preparation therefore in the intraoral cavity.

Optionally, the layers are made from different materials. Alternatively, the layers are made from materials providing different visual properties in the different layers.

Preferably, the machining paths are determined such as to optimize machining time for said material removal operation. Typically, the number of machining paths over any portion of said layer is proportional to the magnitude of the differences between said target dimensional data and said actual dimensional data corresponding to said portion.

Typically, the material removal operation is executed by suitable numerically controlled machining means.

Typically, in step (c) after said operation the or each said parameter associated with the layer substantially conforms with said target dimensional data to within a predetermined tolerance, which may be constant or vary, for example between about ±0.01 mm in some areas and about ±0.1 mm in other areas.

The present invention also relates to a manufacturing system for manufacturing a dental prosthesis from a workpiece having at least one layer of material, the system comprising:

(A) measuring means for providing actual dimensional data for at least one parameter associated with the or each said layer;

(B) microprocessor means for forming, for the or each layer, a comparison between said actual dimensional data and predetermined target dimensional data that it is desired to conform said parameter to for at least one said parameter;

(C) suitable machining means adapted for subjecting the or each said layer to a material removal operation along machining paths which are a function of said comparison, such that after said operation the or each said parameter associated with the or each layer substantially conforms to the target dimensional data.

The system may optionally further comprise material layering means for providing said at least one layer of material. The material layering means is adapted for depositing said layer of material onto a physical model substantially identical to a tooth preparation onto which said prosthesis is to be mounted.

In a first embodiment, said parameter is a geometric parameter comprising surface coordinates of said layer. The actual dimensional data comprises the surface coordinates of said layer prior to said operation.

Preferably, said measuring means comprises a suitable first probe for three-dimensionally scanning the or each said layer. Typically, the first probe provides a three dimensional structure based on confocal imaging. Alternatively, any other suitable means capable of providing a three dimensional surface structure may be employed to obtain the data. The target data is associated with the desired surface profile of the or each said layer for said prosthesis. For an outermost said layer, said target data conforms to a predetermined control volume. The predetermined control volume is defined such as to provide at least one of:

adequate clearance between said prosthesis and adjacent teeth when the prosthesis is fixed onto the corresponding preparation in the intraoral cavity; and adequate occlusion between said prosthesis and teeth of the opposite jaw when the prosthesis is fixed onto the corresponding preparation in the intraoral cavity.

The system may further comprise a suitable library of dental prosthesis and tooth outer surface profiles from which said target data is obtained. Additionally or alternatively, the microprocessor means are adapted for receiving said target data from an external source. Additionally or alternatively, the microprocessor means is adapted to provide said target data. Preferably, the creation of said target data is based on three-dimensionally scanning of the intraoral cavity in the vicinity of the area thereof in which the prosthesis is to be mounted for determining said control volume.

Preferably, a second probe provides a three dimensional structure based on confocal imaging, used in the creation of said target data.

In a second embodiment, the parameter is typically a geometric parameter comprising at least one of the width or height of said layer. The target dimensional data comprises the numerical values of at least one target linear dimension of a location on the jaw on which the crown is to be fitted. The linear dimension is a target width defined such as to provide adequate clearance between said prosthesis and adjacent teeth when the prosthesis is fixed onto the corresponding preparation in the intraoral cavity. Additionally or alternatively, the linear dimension is a target height defined such as to provide adequate occlusion between said prosthesis and teeth of the opposite jaw when the prosthesis is fixed onto the corresponding preparation in the intraoral cavity.

In another embodiment, said parameter is a geometric parameter comprising the profile of a lower edge of said prosthesis. The profile is defined such as to provide close-fitting contact between said prosthesis and the preparation therefore in the intraoral cavity.

Optionally, microprocessor means are adapted for determining said machining paths such as to optimize machining time for said material removal operation. Preferably, the microprocessor means are adapted for providing a number of machining paths over any portion of said layer that is proportional to the magnitude of the differences between said target dimensional data and said actual dimensional data corresponding to said portion.

Preferably, the material removal operation is executed by suitable numerically controlled machining means. The machining means may be adapted for subjecting the or each said layer to a material removal operation along machining paths which are a function of said comparison, such that after said operation the or each said parameter associated with the layer substantially conforms with said target dimensional data to within a predetermined tolerance, which may be constant or may vary between about ±0.01 mm and about ±0.1 mm.

The present invention is also directed to a data creating system for determining target dimensional data of a parameter associated with at least one layer of a dental prosthesis for use in the manufacture thereof, comprising:

measuring means for digitally mapping the intraoral cavity in the vicinity of the area thereof in which the prosthesis is to be mounted;

microprocessor means adapted for:

creating an idealized surface profile for the or each said layer;

manipulating the surface profile to provide target data for the corresponding layer of said prosthesis.

The microprocessor means may be further adapted for determining from the digital map obtained from said measuring means a control volume within which the or each layer of said prosthesis is to fit geometrically and for manipulating the surface profile of the or each layer to fit within the corresponding control volume.

The present invention is also directed to a method for creating target dimensional data of a parameter associated with at least one layer of a dental prosthesis for use in the manufacture thereof, comprising:

(i) digitally mapping the intraoral cavity in the vicinity of the area thereof in which the prosthesis is to be mounted;

(ii) creating an idealized surface profile for the or each said layer; and (iii) manipulating the surface profile of the or each layer provide target data for the corresponding layer of said prosthesis.

The method may further comprise the steps of determining from the digital map obtained from said measuring means a control volume within which the or each layer of said prosthesis is to fit geometrically.

Step (iii) may comprise manipulating the surface profile of the or each layer to fit within the corresponding control volume to provide target data for the corresponding layer of said prosthesis.

The present invention is also directed to a dental prosthesis having at least one finished layer of a material, manufactured according to the method of the invention.

The present invention is also directed to a computer readable medium storing instructions for programming a microprocessor means of a manufacturing system as herein described to perform a method as herein described.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
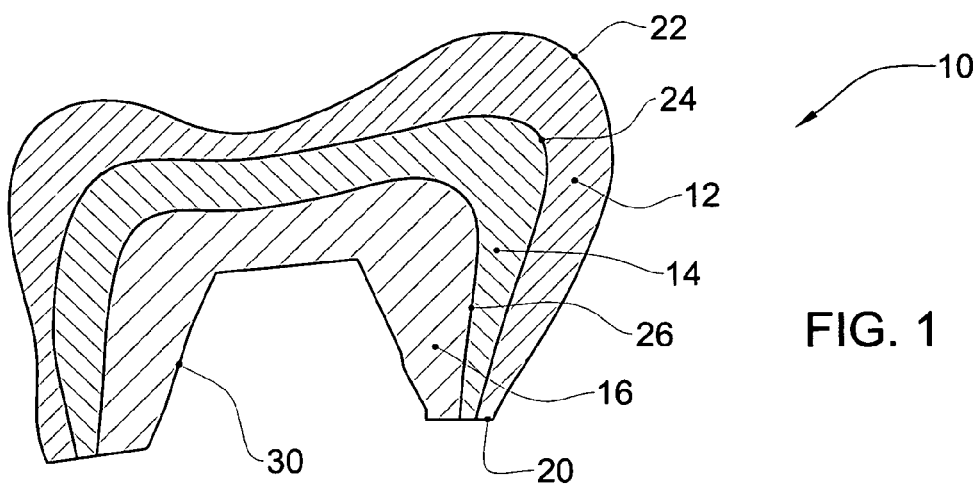
FIG. 1 schematically illustrates in cross-sectional side view the desired construction of a crown prosthesis that it is desired to manufacture according to the first embodiment of the invention.
Figure 2:
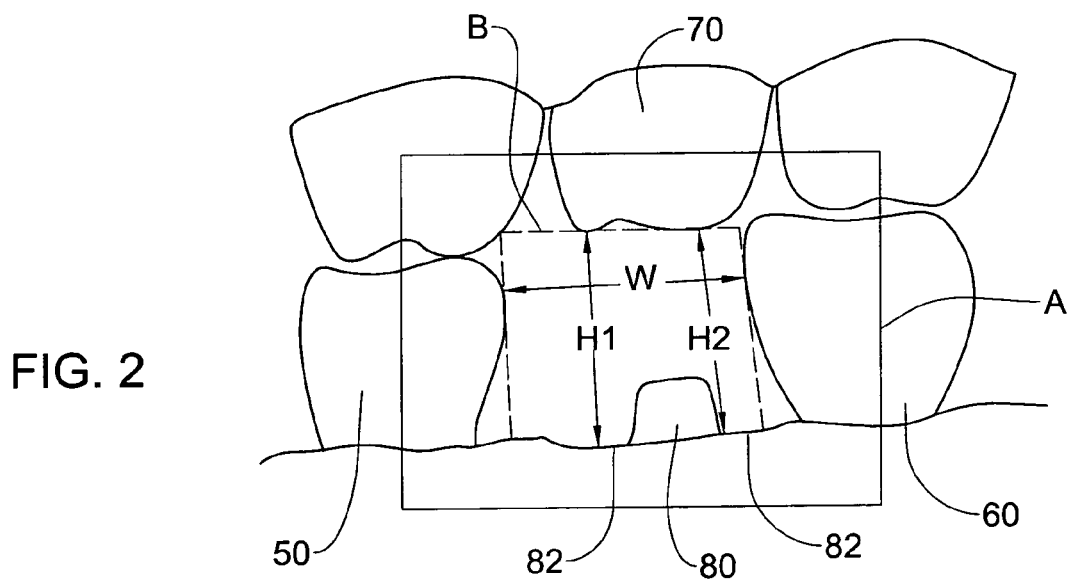
FIG. 2 schematically illustrates in side view the area in the intraoral cavity in which a prosthesis is to be fitted.

In a first embodiment of the present invention, and referring to FIG. 1, in order to manufacture a crown prosthesis, generally designated with the numeral 10, the outer surface 22 thereof is first defined three-dimensionally to provide target dimensional data for a geometrical parameter associated with the layer, in particular the spatial coordinates thereof. The inner surface 30, which is designed to be engaged and bonded onto the preparation may also need to be defined, depending on the manner in which the crown 10 is to be manufactured, as will be described further hereinbelow. In the first place, the shape of the outer surface 22 is chosen according to the function of the tooth that it is replacing: whether it is an incisor, canine, molar, and so on, and the profile chosen must be capable of enabling the prosthesis to carry out the function of the tooth. In addition, the dimensions of the outer surface 22 need to be such as to provide the correct interproximal spacings with respect to adjacent teeth 50, 60, and to provide the proper occlusion with respect to the facing tooth 70 (FIG. 2). Another important factor is that the prosthesis must enable a reasonable insertion path to be established, and if necessary, the shape of inner surface 30 must be modified to provide such a path for the prosthesis.

It may also be desired to manufacture the crown with a series of shells or layers, say three substantially concentric layers, 12, 14, 16, by way of illustrative example. Some crowns may have more than three layers, while others may have less than three, some only a single layer of material. It may sometimes be desired to have a number of layers in order to provide the crown with a natural-looking appearance, in which inner layers may be more opaque than outer layers, for example, or contain a mosaicing of differently colored patches, and/or wherein each layer may be made from a different material. In such cases, it may be of particular importance to control the shape and/or depth of each of the surfaces 26, 24 of the innermost and intermediate layers 16, 14, respectively, and to provide different depths or thicknesses of material as well as different colors at different parts of the crown in order to provide the shading that best matches that of the adjacent teeth.

Figure 10:
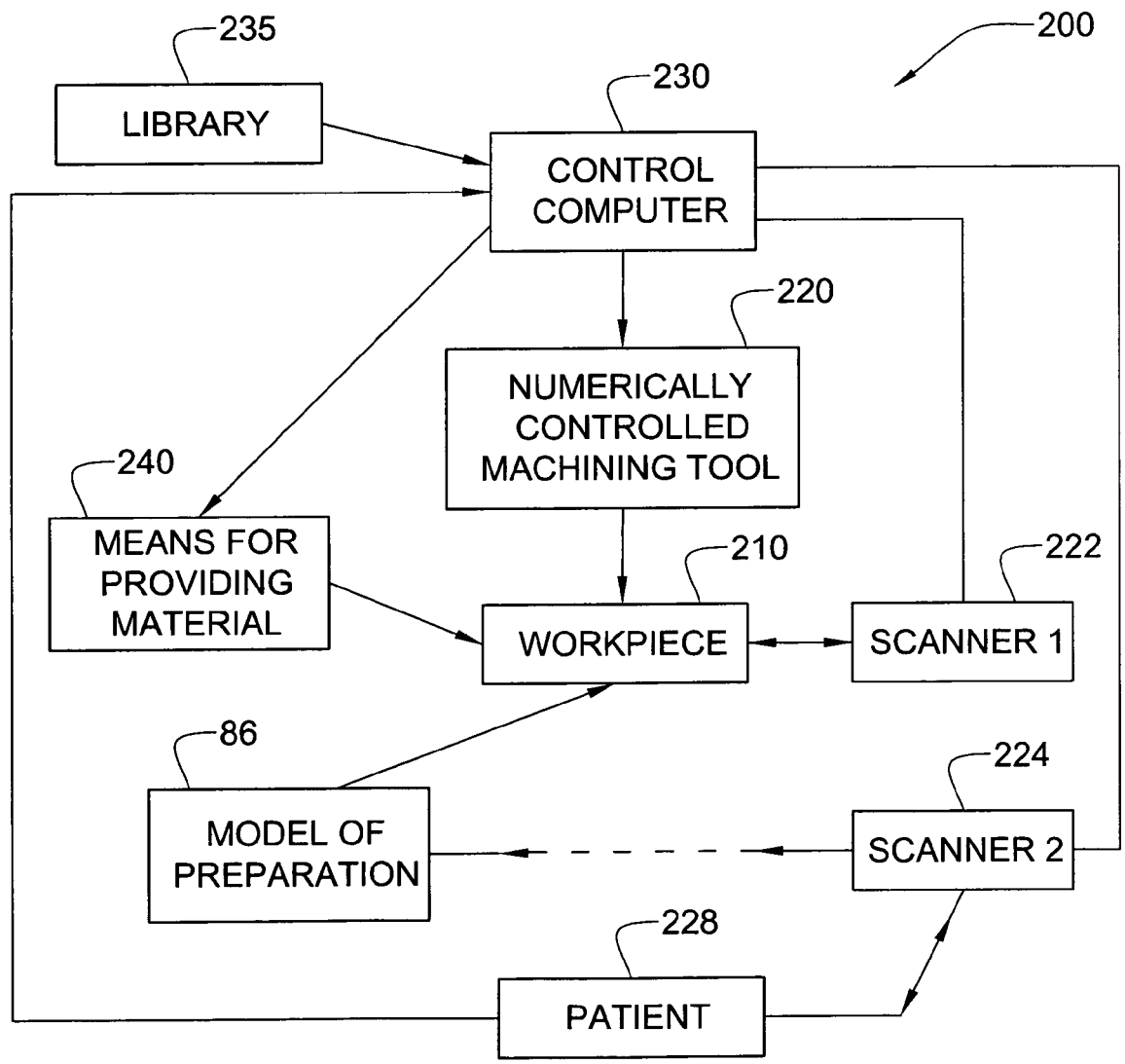
FIG. 10 schematically illustrates the main elements of an embodiment of the system according to the present invention.

Referring to FIG. 10, a system 200 may be used for implementing the method of the invention according to the first embodiment, and other embodiments thereof as will further described herein. The system 200 comprises:

(A) measuring means such as a scanner 222 for providing actual dimensional data for at least one parameter associated with said layer;

(B) microprocessor means such as a controlling computer 230 for forming a comparison between said actual dimensional data and target dimensional data for said layer corresponding to each said parameter, for each said parameter;

(C) numerically controlled machining means 220 adapted for subjecting said layer to a material removal operation along machining paths which are a function of said comparison, such that for each said parameter the actual dimensional data of the parameter after said operation substantially conforms to the target dimensional data.

In the first embodiment, the parameter comprises the relative surface coordinates of the layers—before and after the material removal operation. According to this embodiment, in a preliminary stage of the manufacturing process, and also referring to FIG. 2, target data for the chosen parameter (surface coordinates of the layers) is created. First, a three-dimensional (3D) digital map of the area A of the intraoral cavity in which the crown 10 is to be fitted, is taken. Referring again to FIG. 10, this can be accomplished, for example, with the use of a suitable 3D scanner 224, such as for example by use of a probe that provides a three dimensional structure of a surface based on confocal imaging, for example the confocal probe manufactured by Cadent Ltd under the name of PROSTHOCAD or as disclosed in WO 00/08415, the contents of which are incorporated herein. Alternatively, the 3D digital model may be obtained in any other suitable manner, for example, by any suitable intra-oral scanning method, including contact or non-contact, CT, X-ray means or other means. Alternatively, the 3D model may be obtained from outside the intra-oral cavity by means of a casting or model of the cavity (either the positive or negative model), using any scanning method, including contact or non-contact, CT, X-ray means.

Thus, spatial data regarding at least portions of the adjacent teeth 50, 60 and also of the tooth 70 that is situated opposite to where the crown 10 is to be fitted is obtained, Spatial data is also obtained regarding the preparation 80 (in particular the finish line 82), or of a partial or full implant (not shown) when this partially or fully replaces the preparation 80. From this data a control volume B can be defined including the critical dimensions that the crown 10 needs to conform to, such as the height H1, H2, and width W of the crown, in order to provide a good fit. Then, an outer shape for the crown 10 may be chosen, and this can be accomplished in a number of ways. For example, if the patient 228 has a reasonably healthy tooth on the same jaw but on the adjacent quadrant at a position corresponding to where the crown 10 is to be fitted, this tooth may be scanned to obtain the 3D spatial coordinates thereof. Alternatively, a suitable profile for surface 22 may be chosen and obtained from a library 235 that comprises the 3D spatial profiles of shapes or profiles of the outer surfaces of a plurality of crowns and teeth. If necessary the relative size and shape of the surface may be adjusted by the user to better match the other teeth in the jaw. Then, the chosen surface is adjusted in any suitable manner, either manually, automatically, interactively or in any other manner, in order that the required target dimensions of surface 22 will fit within a control volume B defined in the area A. In particular, the control volume is chosen such as to provide adequate clearance between the crown and adjacent teeth, and adequate occlusion with the opposite teeth, when the crown is properly fixed onto the preparation.

According to predetermined criteria, the details, including shape and size of each of the intermediate surface 24 and 26 can also be chosen or determined, such as are considered that will provide a particular or desired visual effect, for example. Thus, it may be decided, for example, to provide an outer layer 12 made from an opalescent porcelain, but having a varying thickness, so that at some zones the intermediate layer 14 will appear more reflective than at others. Similarly, the intermediate layer 14 can be made from a suitable porcelain having a desired color, and the depth of this layer can also be varied to provide different hues of the color. For example, at places where the depth of the layer 14 is greater, the layer 14 will appear a little lighter than where the layer is shallower.

In this manner, the relative target data, i.e., the desired or idealized spatial coordinates of the surface 26, 24 and 22 to which it is desired the prosthesis to conform to, are created, either manually, automatically, interactively or in any other manner with the aid of a suitable program. This program can be run by control computer 230, or indeed by another computer independent of computer 230, which is adapted for receiving the target data from this independent computer.

Figure 3:
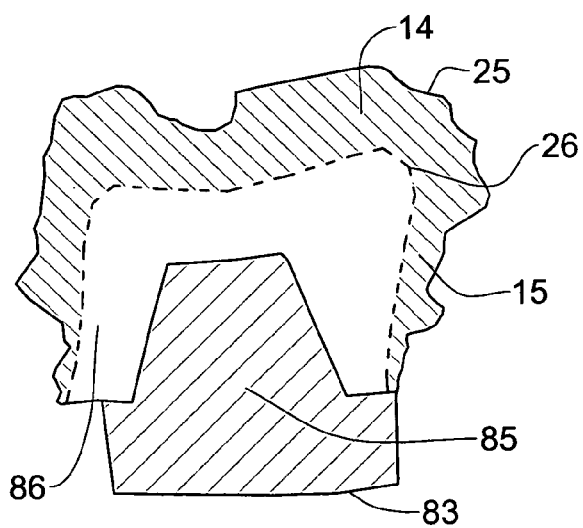
FIG. 3 schematically illustrates in cross-sectional side view a first layer of crown prosthesis of FIG. 1 prior to machining thereof.

In an optional second preliminary stage, and referring to FIG. 3, a physical model 85 of the preparation 80, onto which the crown 10 is to be fitted, is prepared. Referring to FIG. 10, this may be done for example by first preparing a three dimensional digital representation of the preparation by scanning area B of the intraoral cavity of the patient 228, in particular the preparation 80, with scanner 224, and supplying this data to a computer numerically controlled (CNC) machining system, such as a CAD/CAM system for example (indicated by the broken line in FIG. 10), which then machines or mills out the model 86 from a suitable material such as fine grade aluminum oxide, for example. Alternatively, the model 85 may be manufactured in other ways known in the art, for example by casting using a negative model of the preparation 80 as a mould. Typically, the dimensions of the outer surface of model 85 may be increased to take into account the thickness of the adhesive layer that is subsequently to be applied between the inner surface 30 and the preparation 80 itself when the crown is bonded to the preparation. The model 85 typically comprises a graspable lower part 83 for fixing the core with respect to the CNC machine, by means of a suitable jig, for example.

Figure 4:
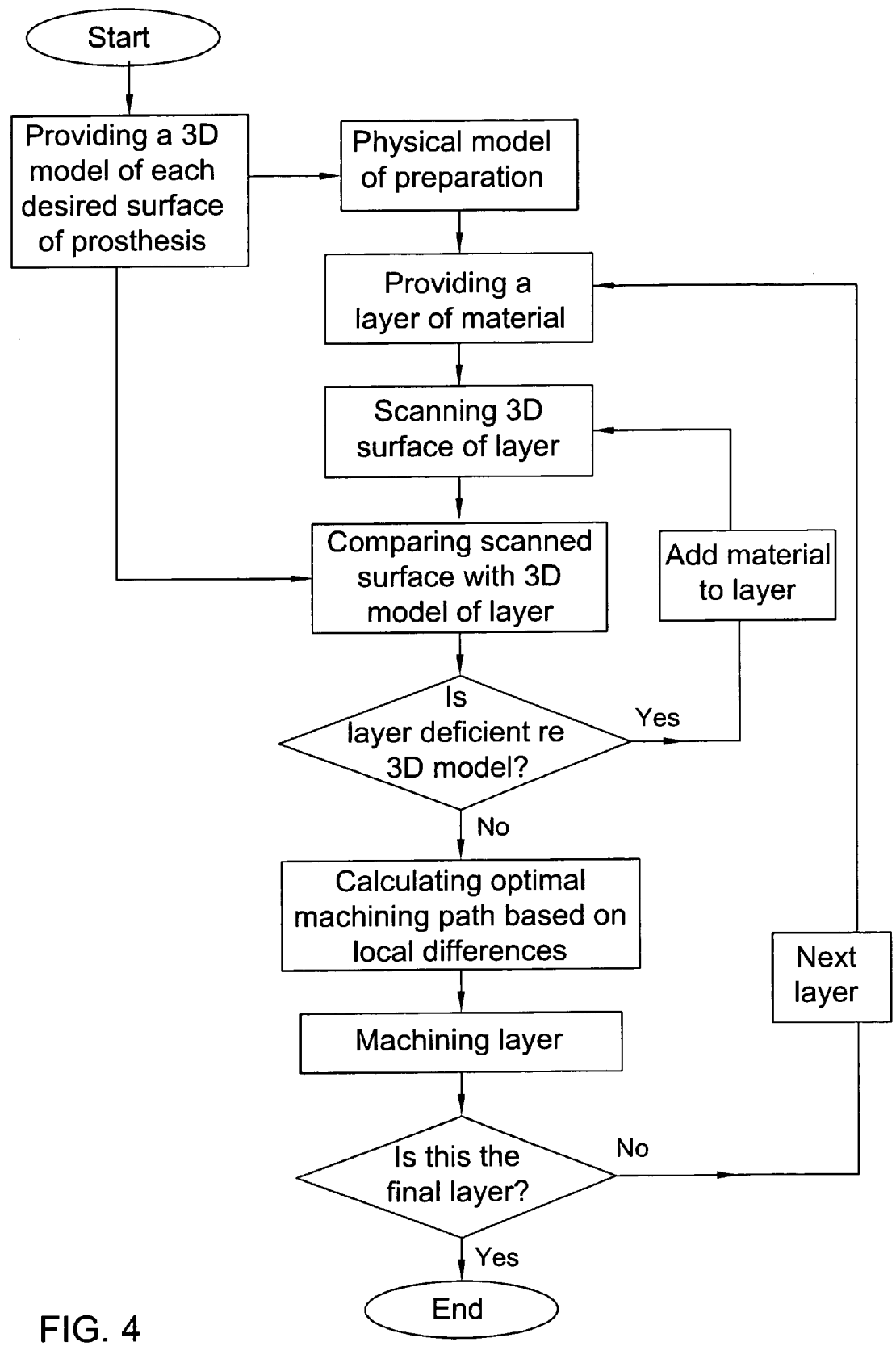
FIG. 4 schematically illustrates a flow chart for manufacturing a crown prosthesis according to the first embodiment of the invention.

Referring to FIG. 3 and FIG. 4, once the idealized 3D model of the surfaces of each layer has been determined, the actual manufacturing process may begin. It is clear that the target coordinates of these surface are created such as to maintain the proper spatial relationship with the model 85. Referring also to FIG. 10, a workpiece 210 is initiated wherein a layer 15 of material is added to the model 85 via suitable means 240, as is known in the art, forming the basis of the innermost layer 16 of the crown. The layer 15 is made from the desired material, such as for example metal or a ceramic having the desired hue, and is deposited or otherwise added in any suitable manner, as is known in the art. Then, the actual dimensional data, i.e., the actual three dimensional spatial coordinates of the outer surface 25 of this layer 15 are determined (relative to a desired datum, such as the coordinates of the surface of the model 85, for example), preferably by means of a 3D scanner 222. In some cases scanner 222 may be physically the same scanner as scanner 224. Generally, though, scanner 222 and scanner 224 are different scanners, since the original 3D mapping of area A may be done at the dental practitioner's clinic, while the scanning of each layer prior to machining and material removal operations is accomplished at the manufacturer of the crown. This dimensional data is then fed to the controlling computer 230 of a suitable CNC machine 220, and the computer 230 then compares the 3D profile of the actual surface 25 with that of the desired target surface 26. The computer 230 then determines the optimal machining paths for removing the excess material 14 on the basis of this comparison to provide an inner layer 16 having surface 26. Thus, the machining paths are specifically tailored to the local differences between surfaces 25 and 26: (a) no time is wasted traversing the machining tool over empty air, (b) more machining paths are provided over areas of the surface 25 which represents greater thickness of material relative to desired surface 26; and, (c) damage is avoided to the tool and to the crown that could otherwise occur from attempting to machine too much material at some locations. Thus, each layer is subjected to a material removal operation by the numerically controlled machining means along machining paths which are a function of said comparison, such that for each parameter the actual dimensional data of the parameter after this operation substantially conforms to the target dimensional data.

The CNC machine may remove the material necessary to provide the desired topography of the layer in one pass thereof, or in several passes thereof, depending on the thickness of the layer relative to the desired target surface thereof. In the case where several passes are necessary, all the passes may be calculated from the original scan, taking into account the depth of each pass. Alternatively the layer may be scanned after each pass, and the machining path calculated for the next pass for the same layer.

A next layer of material may then be provided in any suitable manner over the newly machined layer 26, as is known in the art, and the new layer scanned to provide the 3D spatial data thereof to the computer, which compares this with the desired surface 24. In a similar manner to that described before, the optimal machining path for arriving at surface 24 is computed and subsequently executed. The same procedure is repeated for as many layers are necessary or desired, until the final surface 22 is machined for the crown 10.

Of course, in prostheses made from a single piece of material, there is effectively only a single layer, and this layer is scanned and machined in a similar manner to that described above, mutatis mutandis.

Referring to FIG. 4, every time a new layer is added, it may be automatically checked, by the subsequent 3D scanning via scanner 222, that there is enough new material to fill the required thickness at every location in the layer. In this manner, if the layer is deficient in relation to the target 3D dimensional data, e.g., there are pockets in the layer (before machining) where insufficient material has been applied, more material may be added, and the system 200 advises the operator where the deficiency is to be found in the layer. Suitable display means can be utilized for illustrating the location of the deficiency. The layer is then re-scanned prior to determining the optimal machining paths and commencing machining. At the same time, no machining time is wasted traversing the machining head over empty air where there is no material, and material removal may be maximized at each and every machining path, since these are designed to precisely match the characteristics of the actual layer of the material present, and not a fictitious envelope thereof.

Optionally, at the end of the machining of each layer, and preferably at least after the machining of the final layer, the outer surface of the layer is scanned and compared with the expected profile of the layer. If the actual layer is within a predetermined tolerance, then the machining operation is considered complete for the layer. If the layer is not within tolerance, this may indicate that perhaps the tool got damaged and/or that the crown may have moved doing the machining process, and further investigation may be warranted. The actual acceptance tolerance value may be fixed or may actually vary over the surface of the layers, particularly the final outermost layer. For example, a tolerance of ±0.01 mm may be acceptable for critical dimensions such as the lower edge 20 of the crown or the mesiodistal size W, while a tolerance of 0.1 mm may sufficient elsewhere.

In a variation of this embodiment, optionally, a coping, typically made from a suitable metal or ceramic, may be manufactured first, using any suitable method, and then mounted onto a model of the preparation or onto a suitable strut. Then, layers of material are added, scanned and machined, as described above, mutatis mutandis.

Figure 5:
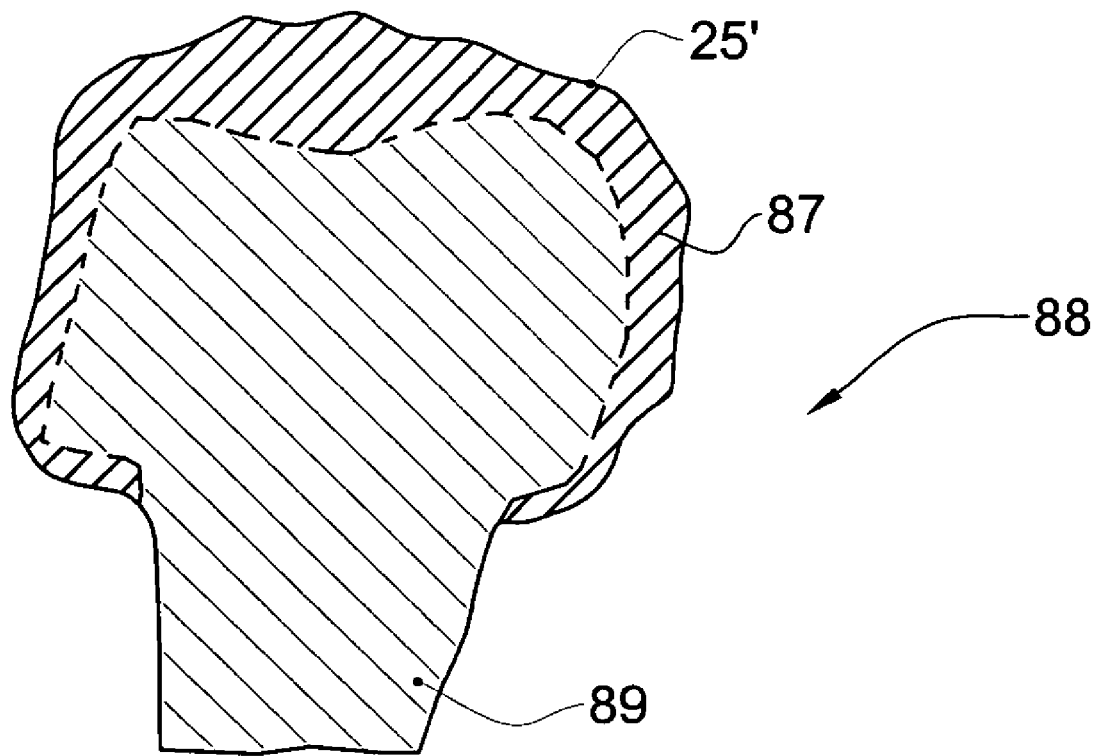
FIG. 5 schematically illustrates in cross-sectional side view a core used to provide the first layer of crown prosthesis, prior to being subjected to a material removal operation.
Figure 6:
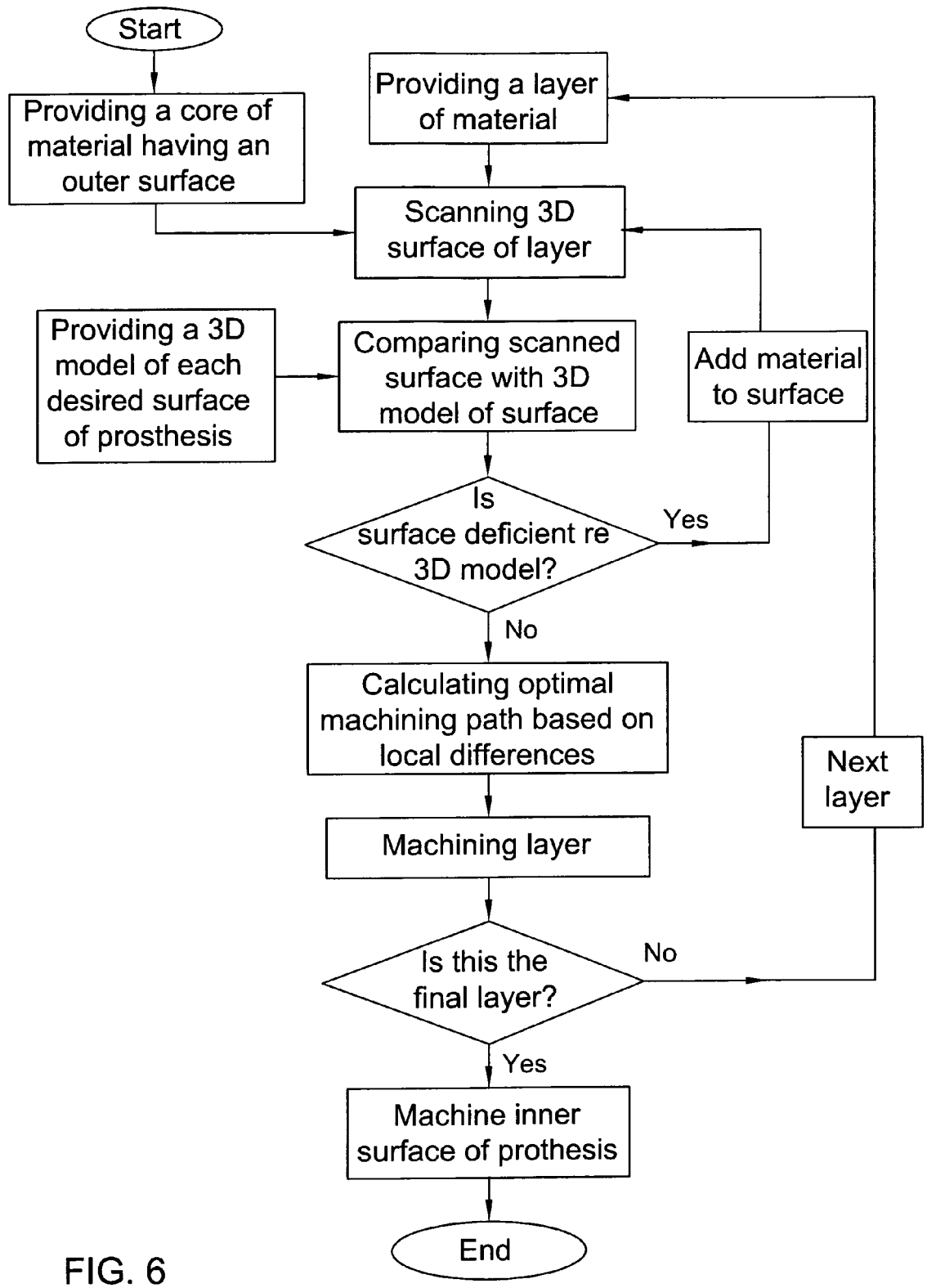
FIG. 6 schematically illustrates a flow chart for manufacturing a crown prosthesis according to a variation of the first embodiment.

Alternatively, and referring to FIG. 6, it is possible to omit the second preliminary stage, and to prepare the inner surface 30 at the end of the manufacturing process. In such a case, the first stage in the manufacturing process, and referring to FIG. 5, is to provide a workpiece in the form a core 88 of a suitable material, having a graspable lower part 89 for fixing the core with respect to the CNC machine, by means of a suitable jig, for example. Alternatively, the core may be provided with a well (later to be machined to conform to the outer shape of the preparation), and the core supported on jig via a strut that is temporarily glued or otherwise mounted to the well. The core may be provided, for example, by casting using a universal mould that is suitable in size and shape for the particular application. The upper part 87 of the core 88 is to form the basis of the first layer 16, and a scan of the outer surface 25' is taken, compared with the digitized 3D model of the required layer 26, and the optimal machining paths computed and executed, in a similar manner to that described above, mutatis mutandis. Additional layers may be added as described before, to provide ultimately the final outer surface 22 of the crown 10. Then, an additional step is provided, which is to remove the lower part 89, and to machine instead a cavity corresponding to the required inner surface 30, as well as the lower edge 20 from the digitized 3D data in the computer. The lower edge 20 is substantially complementary to the finish line 82 of the preparation.

The profile of lower edge 20 of the crown 10 may be brought into conformity with a target data for the profile (i.e., the spatial coordinates corresponding to the profile of the finish line 82 of the preparation) in a similar manner to the rest of the crown 10, and may in fact be defined as being part of the surfaces of the layers. Thus, the differences between the actual measured profile of the lower edge 20 of the workpiece and the target profile of the finish line 82 of the preparation are determined, and suitable machining paths are computed. The lower edge 20 of the crown 10 may be machined in stages, concurrently with the machining of each layer, or as a finishing operation including all the layers after these have been subjected to corresponding material removal operations to provide the desired external profiles. Of course, the spatial relationship of the lower edge 20 with respect to other critical dimensional parameters of the crown 10 needs to be defined, so that the crown 10 will still properly fit within the control volume B.

Figure 7:
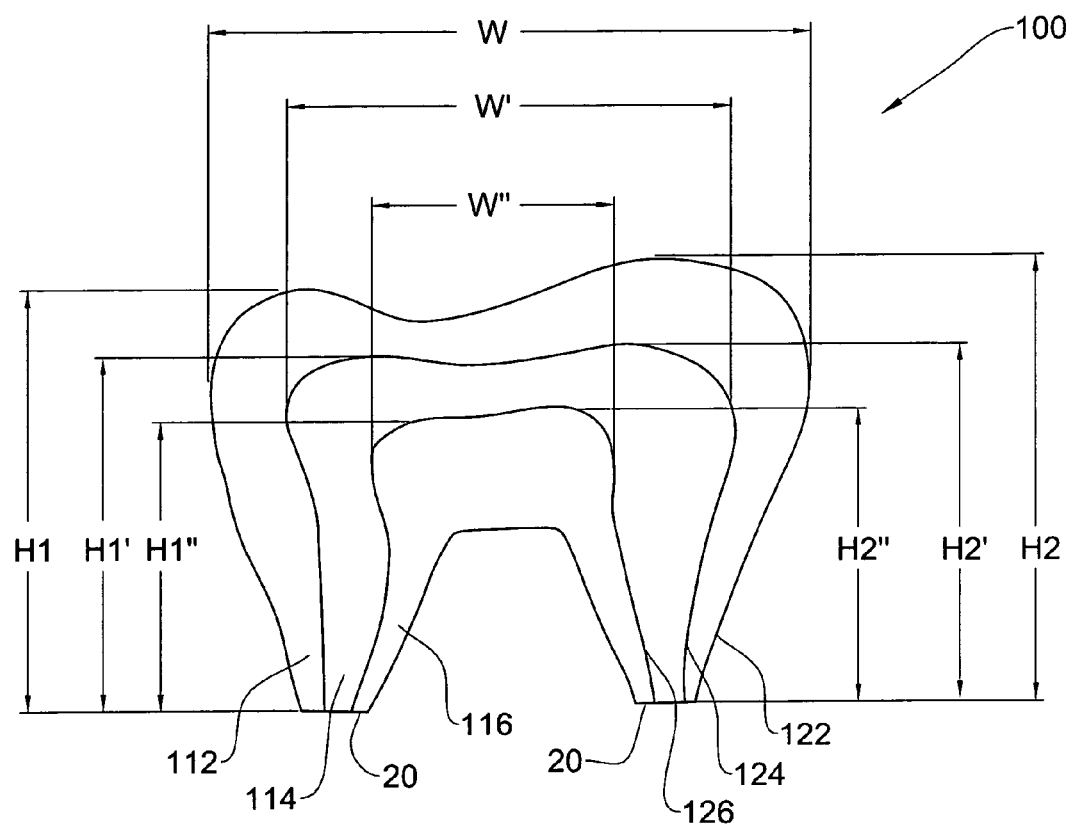
FIG. 7 schematically illustrates in cross-sectional side view the desired construction of a crown prosthesis that it is desired to manufacture according to the second embodiment of the invention.
Figure 8:
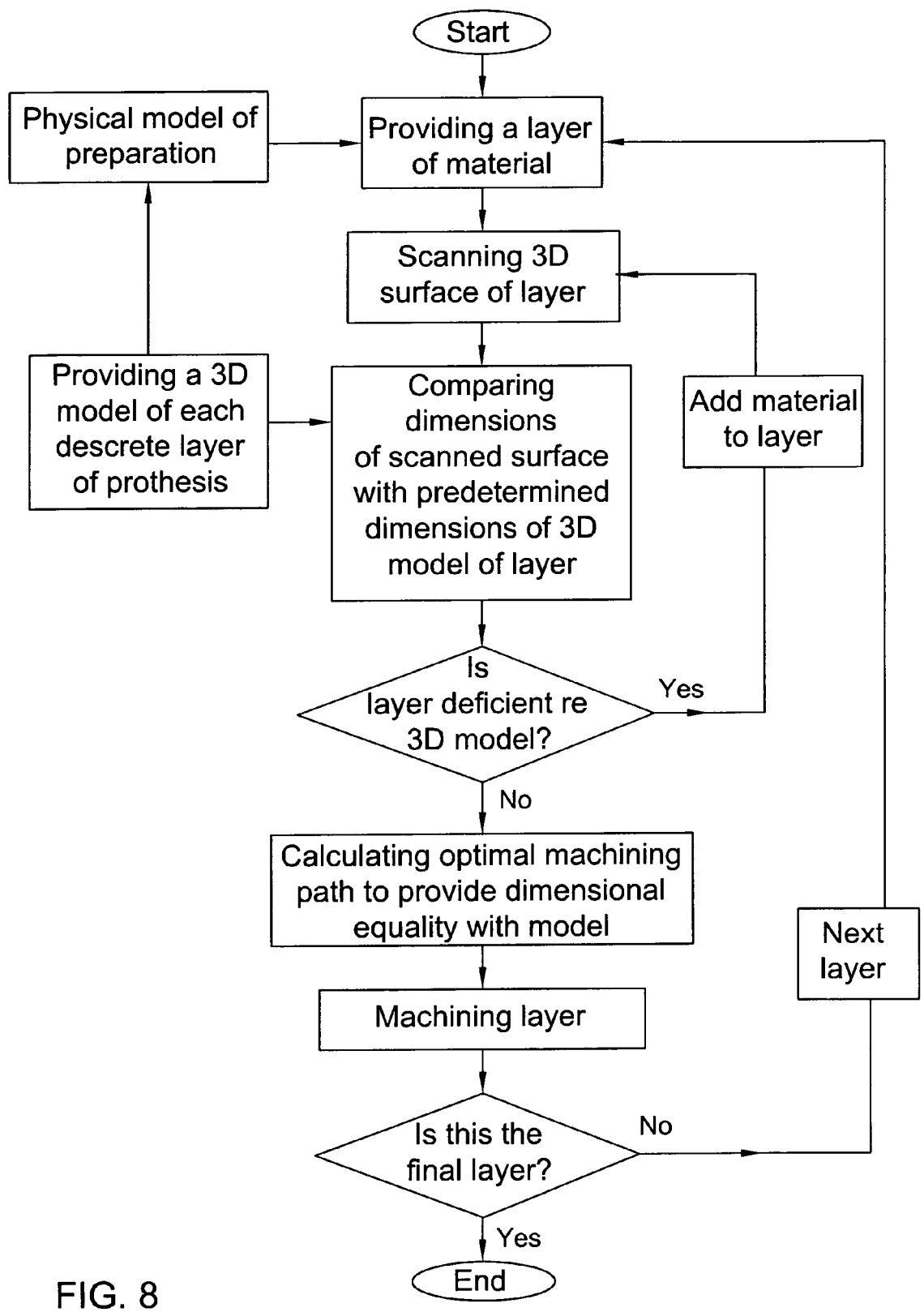
FIG. 8 schematically illustrates a flow chart for manufacturing a crown prosthesis according to the second embodiment of the invention.

Referring to FIG. 7 and FIG. 8, in another embodiment of the present invention, the crown 100 is manufactured according to a more simplified procedure, in which compliance to one or more predetermined linear dimensional parameters is required, rather than of the full 3D geometry. In particular, and referring to FIG. 2, it is required that the prosthesis 100 have the necessary dimensions to fit properly within the control volume B. For example, the following three parameters may be sufficient to define dimensional compliance with control volume B:

the mesiodistal size W of the crown, i.e., the predicted distance and direction between the interproximal contact points with the adjacent teeth 50, 60;

characteristic heights H1, H2 between the finish line 82 of the preparation and the cuspal area of the crown, at least at two locations, such as to provide optimal occlusion with the facing tooth 70;

a characteristic buccal-lingual dimension (not shown).

A similar system to the system 200 described above may be used to implement the second embodiment of the method of the invention, mutatis mutandis. As for the first embodiment described above, the 3D spatial data of the control volume B and of the surrounding teeth may also be obtained using a suitable 3D probe, for example. Advantageously, a probe for determining three dimensional structure by confocal focusing of an array of light beams may be used, for example as manufactured under the name of PROSTHOCAD or as disclosed in WO 00/08415. From the 3D digital model created from this data, the critical dimensions of parameters W, H1 and H2 are determined. Alternatively, the dimensional data for the critical parameters may be determined in a different manner, such as for example direct measurement within the area A, or indirectly by performing measurements on a physical model of the patient's teeth including area A, though this tends to be less accurate than using the 3D digital model.

If it is desired to manufacture the crown 100 from a plurality of layers, e.g., layers 112, 114 and 116 of FIG. 7, the values of the parameters W, H1, H2 can be correspondingly adjusted for the intermediate and inner layer surfaces, 124 and 126, respectively, according to the desired thicknesses of the intermediate layer 114 and inner layer 116, or, alternatively, different dimensional parameters may be chosen for each of these layers. These target dimensions will be designated herein as W', H1', H2' for intermediate layer 114, and W", H1", H2" for inner layer 116, corresponding to the target dimensions W, H1, H2, respectively, of the outer layer 112.

Figure 9:
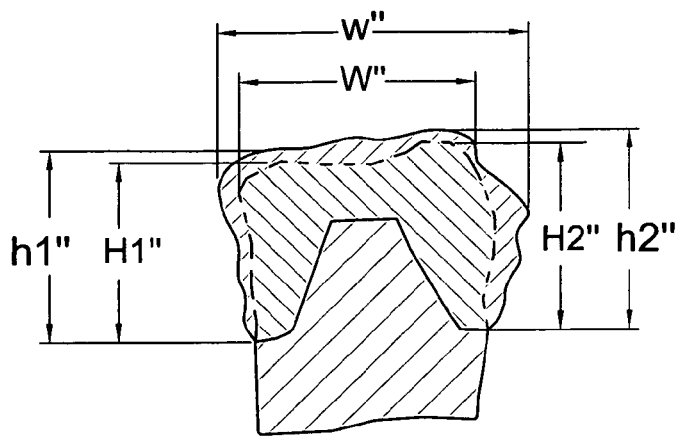
FIG. 9 schematically illustrates in cross-sectional side view a first layer of crown prosthesis of FIG. 7 prior to machining thereof.

In the next step of the process, and referring to FIG. 8, a crown is manufactured, starting with either a physical model 85 of the preparation on which a first layer of material is added, or alternatively with a core, in a similar manner to that described herein with respect to the first embodiment, mutatis mutandis. Then, and referring to FIG. 9, the dimensions of the first layer 115 of material along directions corresponding to W", H1" and H2" are taken, yielding w", h1" and h2".

In the next stage of the process, the measured actual dimensions w", h1", h2" are fed to a suitable computer, as are the desired or target dimensional values for the parameters W", H1" and H2", and the computer is then able to work out suitable, and preferably optimal, machining paths for removing material from the layer 115 to as to equalize the measured dimensions w", h1", h2" with respect to the required target dimensions of the parameters W", H1" and H2". The manner in which material is removed from the rest of the surface 26 may not necessarily be so critical, and the control computer may design generalized machining paths so as to provide a relatively smooth profile for surface 26 within the envelope defined by W", H1", H2", such as to provide a reasonable shape to the prosthesis.

Similarly, more material may then be added to the inner layer to form an intermediate layer, and the dimensions of the new layer, w', h1', h2', are determined and compared with the dimensions of the critical parameters W', H1', H2'. In a similar manner to the inner layer, the intermediate layer may also be machined in such a manner as to provide compliance with the desired values of the critical parameters. Finally, the outer layer is provided in a similar manner to the intermediate and inner layers, mutatis mutandis.

While the above manufacturing procedures have been described with respect to a crown having three layers, they are applicable, mutatis mutandis, to crowns having more than three layers or less than three layers, in particular to crowns made from a single layer of material.

According to the present invention, the lower edge of a crown may also be machined in an optimal manner. Optionally, and referring to FIGS. 1, 2 and 3, the spatial coordinates of the target finish line 82 are scanned as described herein. Then, the spatial coordinates of the actual lower edge 20 of the crown prosthesis, which may have been prepared according to the present invention or in any other manner, are determined in a similar manner as hereinbefore described, mutatis mutandis to provide target data for the profile parameter associated with the finish line. A suitable controlling computer then determines the differences between the actual and target geometrical profiles, works out suitable machining paths and sends appropriate commands to a CNC machine coupled to the computer.

For each embodiment of the invention, it is important that the spatial orientation of the crown at every point of its manufacture is always maintained with respect to some datum reference, so that all the critical dimensions are always obtained along directions corresponding to the directions along which the original parameters were defined for each layer.

For every embodiment, the machining paths are determined by the controlling computer preferably such as to optimize machining time for said material removal operation. Preferably, the number of machining paths over any portion of each layer during the material removal operation is proportional to the magnitude of the differences between said target dimensional data and said actual dimensional data corresponding to the portion. Thus, where there is a large thickness of material that needs to be removed, more machining paths are provided than at other places where there is less excess material.

While the embodiments have been described herein in the context of a crown prosthesis, other dental prostheses, such as for example bridges or caps, may be manufactured in a similar manner thereto, mutatis mutandis.

Optionally, all the activity required for providing the prosthesis may be carried out at one location. Alternatively, different parts of the activity may be carried out at different locations. When the activity is carried out in different locations, each party (e.g., the dental practitioner and the technicians that manufacture the prosthesis) need to communicate at least two types of information: (a) the prescription—requests regarding the required prosthesis; and (b) computer files relating to the model of the intra-oral cavity, including the prescription, and other information such as the finish line, color and coloring schemes for the required restoration or prosthesis. The communication of the information may be executed in any manner, including for example via data transfer means between electronic systems that may be remote one from the other, or via physical media, including storing media such as for example, CD, DVD, flash memory, and so on, capable of storing the required information, typically in digital form For example, and as is clear from the foregoing, a data creation system and method can also be provided, independently of the manufacturing system and method, for creating the target data for each parameter and for each layer of the prosthesis. Thus, the target data, which represents the desired state of the parameters of the prosthesis after manufacture thereof can be obtained at one location, such as for example the dentists' clinic or a laboratory associated therewith, and the manufacturing process can be carried out elsewhere. The data creation system thus comprises:

measuring means, such as scanner 224, for digitally mapping the intraoral cavity in the vicinity of the area thereof in which the prosthesis is to be mounted;

microprocessor means such as computer 230 or another computer, for example, in which the microprocessor means is adapted for:

determining from the digital map obtained from said measuring means a control volume within which the or each layer of said prosthesis is to fit geometrically;

creating an idealized surface profile for the or each said layer;

manipulating the surface profile of the or each layer to fit within the corresponding control volume to provide target data for the corresponding layer of said prosthesis.

The present invention also includes a computer-based product which may be hosted on a storage medium and include instructions which can be used to program a microprocessor such as computer 230 to perform a process in accordance with the present invention. This storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

In the method claims that follow, alphanumeric characters and/or Roman numerals or the like used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

The invention claimed is:

1. A method for manufacturing a dental prosthesis having a layer of material, said prosthesis for mounting in an intraoral cavity, the method comprising:
 (i) digitally mapping at least an area of the intraoral cavity in which the prosthesis is to be mounted;
 (ii) creating an idealized three-dimensional surface profile for said layer based on a digital map provided in (i);
 (iii) providing said layer of material on a workpiece, said layer of a material comprising an outer surface;
 (iv) for said layer of material:
  performing a mapping operation to determine a three-dimensional shape of said outer surface of the corresponding layer of material;
  subjecting said layer of material to a material removing operation comprising machining paths to form the corresponding prosthesis layer;
  wherein the machining paths are computer-controlled on the basis of local differences between said three dimensional shape and said idealized three-dimensional surface profile for the corresponding said layer, and optimized to reduce machining times.

2. A method as claimed in claim 1, wherein step (iii) is implemented prior to step (i).

3. A method as claimed in claim 2, wherein said layer of material is a first, innermost layer of material deposited onto a physical model substantially identical to a tooth preparation onto which said prosthesis is to be mounted.

4. A method as claimed in claim 3, further comprising the step of:
 (v) providing an additional layer of material over said layer after step (iv);
 (vi) creating an idealized three-dimensional surface profile for said additional layer;
 (vii) for said additional layer of material:
  performing a mapping operation to determine a three-dimensional shape of the outer surface of said additional layer of material;
  subjecting said additional layer of material removing operation comprising machining paths to form the corresponding prosthesis layer;
  wherein the machining paths are computer-controlled on the basis of local differences between said three-dimensional shape of said outer surface of said additional layer and said idealized three-dimensional surface profile for said additional layer, and optimized to reduce machining times.

5. A method as claimed in claim 4, wherein said prosthesis comprises a plurality of further additional layers.

6. A method as claimed in claim 5, further comprising repeating steps (v) to (vii) for each one of said plurality of further additional layers.

7. A method as claimed in claim 5, wherein said layers are made from different materials.

8. A method as claimed in claim 5 wherein said layers are made from materials providing different visual properties in the different layers.

9. A method as claimed in claim 2, wherein said layer is a last, outermost layer of said prosthesis.

10. A method as claimed in claim 1, further comprising the step of: providing idealized data for said idealized three-dimensional surface profile prior to step (ii).

11. A method as claimed in claim 9, wherein the number of machining paths over any portion of said layer is proportional to the magnitude of the differences between said idealized data and said actual data corresponding to said portion.

12. A method as claimed in claim 1 wherein said prosthesis comprises one said layer.

13. A method as claimed in claim 1, wherein said material removal operation is executed by suitable numerically controlled machining means.

14. A method as claimed in claim 1, wherein in step (iv) after said operation said three dimensional shape associated with the layer substantially conforms with said idealized three-dimensional surface profile to within a predetermined tolerance.

15. A method as claimed in claim 14, wherein said tolerance may vary between about ±0.01 mm and about ±0.1 mm.

16. A dental prosthesis having at least one finished layer of a material, manufactured according to the method of claim 1.

17. A manufacturing system for manufacturing a dental prosthesis from a layer of material, the system comprising:

(a) first scanner adapted to digitally map at least an area of an intraoral cavity in which the prosthesis is to be mounted;

(b) first microprocessor system adapted to create an idealized three-dimensional surface profile for said layer based on a digital map provided by said first scanner;

(c) material adding system adapted to apply said layer of material on a workpiece, said layer of a material comprising an outer surface;

(d) second scanner adapted to perform a mapping operation to determine a three-dimensional shape of said outer surface of said layer of material;

(e) machining system adapted to subject said layer of material to a material removing operation comprising machining paths to form a corresponding prosthesis layer, said machining paths being computer controllable;

(f) second microprocessor system adapted to control said machining paths on the basis of local differences between said three-dimensional shape and said idealized three-dimensional surface profile for the corresponding layer, and optimized to reduce machining times.

18. A manufacturing system according to claim 17 wherein said first scanner and said second scanner constitute a common scanner.

19. A manufacturing system according to claim 18 wherein said first microprocessor system and said second microprocessor system constitute a common microprocessor system.

20. A manufacturing system according to claim 17 wherein said first microprocessor system and said second microprocessor system constitute a common microprocessor system.

* * * * *